United States Patent [19]
Gordon et al.

[11] Patent Number: 5,558,918
[45] Date of Patent: Sep. 24, 1996

[54] PRESSURE BANDAGE TO AVOID EXPOSURE TO BLOOD BORNE PATHOGENS

[76] Inventors: Chrisanne Gordon; George W. Waylonis, both of 2310 Hoxton Ct.; John G. Dirina, 3828 Norbrook Dr., all of Columbus, Ohio 43220

[21] Appl. No.: 355,496

[22] Filed: Dec. 14, 1994

[51] Int. Cl.[6] .................... A61F 13/00; A61L 15/00
[52] U.S. Cl. .................. 428/100; 428/167; 428/182; 428/186; 428/192; 428/194; 428/212; 428/213; 428/354; 602/41; 602/42; 602/58; 602/62
[58] Field of Search .................. 428/100, 192, 428/194, 212, 213, 354, 167, 182, 186; 602/41, 42, 58, 62

[56] References Cited

U.S. PATENT DOCUMENTS

| | | | |
|---|---|---|---|
| 2,273,873 | 2/1942 | Klein | 602/42 |
| 3,520,306 | 7/1970 | Gardner | 602/58 |
| 4,212,296 | 7/1980 | Schaar | 602/42 |
| 4,677,974 | 7/1987 | Leonardi | 602/42 |
| 5,135,518 | 8/1992 | Vera | 602/52 |
| 5,376,067 | 12/1994 | Daneshvar | 602/58 |

*Primary Examiner*—Nasser Ahmad

[57] ABSTRACT

A multi-layered bandage is disclosed, for preventing or reducing transmission of blood borne pathogens from a bleeding wound area to a person applying the bandage to the wound, having a non-porous first layer having a first side and a second side opposite the first, the first side of the non-porous first layer serves as a gripping means or mitten whereby the hand of the person applying the bandage is prevented from contacting blood from the wound; a gauze pad second layer having a first side and a second side opposite the first, the first side of the gauze pad affixed to the second side of the non-porous layer; a flexible strap, of substantial longitudinal elasticity to allow the strap to extend and wrap around the wound area and be secured, having a first side and a second side opposite the first and having a first end affixed to the first side of the non-porous layer and a second end opposite the first; and a fastening means affixed to the second end of the strap and constructed of material to allow the strap to retain and compress the bandage on the wounded area.

24 Claims, 3 Drawing Sheets

PRESSURE BANDAGE TO AVOID EXPOSURE TO BLOOD BORNE PATHOGENS

CROSS REFERENCES TO RELATED APPLICATIONS

There are no prior applications on the basis of which priority is being claimed, the identity of which must be identified in accordance with 37 C.F.R. §1.78 and Section 201.11 of the M.P.E.P.

STATEMENT AS TO THE RIGHTS TO INVENTION §310 M.P.E.P.

No Federally sponsored research and development was involved in the invention that is the subject of this application.

BACKGROUND OF THE INVENTION

1. Field of the Invention

The present invention relates to the field of products for use in emergency medical treatment and, more specifically, for use in emergency applications of pressure bandages to a bleeding wound while preventing the person applying the bandage from coming into contact with blood from a wound.

This invention comprises a multi-layer bandage which can be quickly and safely applied to a wound in such a manner that the risk of exposure by the bandage applicant to blood borne pathogens from a wound is avoided or substantially reduced when administering first aid.

2. Description of the Prior Art

The risk of a person contracting a blood borne disease from exposure to another's blood has increased dramatically. For example, recent articles state that, worldwide, the number of cases of acquired immune deficiency syndrome ("AIDS") has risen 60% during the period from July, 1993 to July, 1994. See, Maugh, "Outlook is Pessimistic at AIDS Conclave," *Los Angeles Times*, p. 1, Col. 5, (Aug. 8, 1994). The World Health Organization estimates that the total number of individuals infected with the "human immune deficiency virus" is 17 million. Exposure to AIDS in the workplace can be particularly problematic. For example, an estimated 37 percent of major U.S. employers have dealt with actual or perceived cases involving employees who had either HIV, the human immunodeficiency virus, or AIDS. This is a 65 percent increase from the 1989 figures. See, Klein, et al. "With more businesses having to accommodate HIV-positive employees, companies need guidelines to address federal disability laws and privacy rights," *The New York Law Journal*, p. B5 (May 9, 1994). More than two-thirds of companies with 2,500 to 5,000 employees report that they have employed at least one HIV-positive employee, and 1 in 12 companies with 500 or fewer employees say that they have employed someone with the HIV infection in the workplace.

In the manufacturing workplace, accidents occur which could result in an employee receiving a wound injury that requires immediate on-site bandaging to staunch the wound's bleeding until it can be later treated in a medical setting. Often, the emergency aid must be administered by person other that the wounded party or victim. However, the person or "good Samaritan" applying this emergency bandaging is exposed to the blood from the victim during the process of applying the bandage to the wound. Thus, there is a potential risk of exposing the person applying emergency aid to the victim's blood and further risk of the applicant contracting any HIV infection from a blood borne pathogen found in the victim's blood. Because of these risks, workers often are reluctant to provide aid to a bleeding co-worker because they are afraid of exposure to blood borne pathogens.

This concern about exposure to blood borne pathogens is now a matter of federal regulation. See, *OSHA Bloodborne Pathogens Regulations*, 29 C.F.R. 1910, 1030 (1993). Under these regulations, the Occupational Health and Safety Administration requires employers to protect employees from HIV and AIDS exposure. Indeed, employers whose employees may be exposed to blood are required to prevent HIV transmission by providing protective gear and implementing written exposure plans and work practices that minimize exposure. A similar concern applies in many other environments, other than the workplace, where such exposure can occur.

Previously, most commercially available bandage products for use in administering emergency aid to a bleeding wound were in the form of gauze type bandages. Gauze products are porous and absorbent by their nature, and the person who is administering such an emergency aid gauze bandage is at risk of exposure to the victim's blood as it absorbed through the porous gauze. Prior to this invention it has been the usual practice for industries to make available to its employees protective gloves to use in conjunction with applying bandage gauze. However, this combination of having the bandage applicant don gloves prior to administering aid is not ideal. Often, the gloves are not immediately available or accessible because of either their location or an oversight in keeping emergency aid stations properly supplied. The gloves and gauze must be purchased and stocked separately, thereby increasing the cost for such protective measures. The use of a glove and gauze combination is cumbersome and significantly increases the time it takes for a person to administer emergency aid to a victim. For example, some gloves are difficult to put on, particularly when the user is excited as result of the emergency conditions. The person must first unwrap and then put on the gloves. Only then can the person unwrap the gauze and safely administer first aid. The separate glove and gauze combination further requires the person administering aid to maintain hand to wound pressure until the gauze can be secured on or about the wound by some other means, such as surgical tape. Gloves also have additional problems, in that certain individuals suffer negative allergic reactions from wearing the gloves.

An invention is needed that will allow an injured person to receive emergency care quickly while at the same time protecting the person giving the care from the risk of contracting a blood borne disease. The invention must comprise all of the useful elements of gauze, gloves and tape into a single product. An invention is needed which would enable the bandage to be secured and pressed against the wound without the need of additional supplies such as surgical tape. An invention is needed in which the emergency bandage can be manufactured inexpensively. A solution to this problem is an emergency pressure bandage which can be applied quickly to the wound, protect the person applying the bandage from exposure to a bloodborne pathogen, and can be secured in a manner that maintains bandage pressure on the wound. The present invention provides the means by which a material that is impermeable to blood comprises the top layer of the bandage, thereby preventing the blood from penetrating the bandage and contacting the person applying the bandage. This top layer of the bandage also provides a holding means which enables the person administering first aid to grasp the bandage quickly and safely and to protect the user's hand while applying the bandage; the impermeable layer protects the portion of the hand and fingers touching the bandage from exposure to blood by preventing blood from penetrating the bandage. Unlike compression bandages and the thin plastic used in commercial, over-the-counter bandages, the invention's impermeable layer must be flexible enough to conform to the wound area, yet it must have, as a secondary benefit, sufficient stiffness to apply pressure to the wound. One or more straps affixed to the top layer of the bandage can be wrapped and secured around the wound area, which enables the bandage to serve as a compress over the wound. A gauze pad is the bottom layer of the bandage and is the layer that is applied onto the wound. As noted above, in the case of larger bandages for use on larger wounds, a non-porous sleeve is provided into which one hand of the person applying the bandage can be inserted, and the bandage held in place, while the straps are secured. The sleeve would provide further protection from blood to the back and sides of the hand of the person applying the bandage.

SUMMARY OF THE INVENTION

The bandage is a multi-layered device having a non-porous first layer having a first side and a second side opposite the first the first side of the non-porous first layer serves as a gripping means whereby the hand of the person applying the bandage is prevented from contacting blood from the wound, a gauze pad second layer having a first side and a second side opposite the first, the first side of the gauze pad affixed to the second side of the non-porous layer, and a flexible strap having a first side and a second side opposite the first and having a first end affixed to the first side of the non-porous layer and a second end opposite the first.

DETAILED DESCRIPTION OF THE INVENTION

Figure 1:
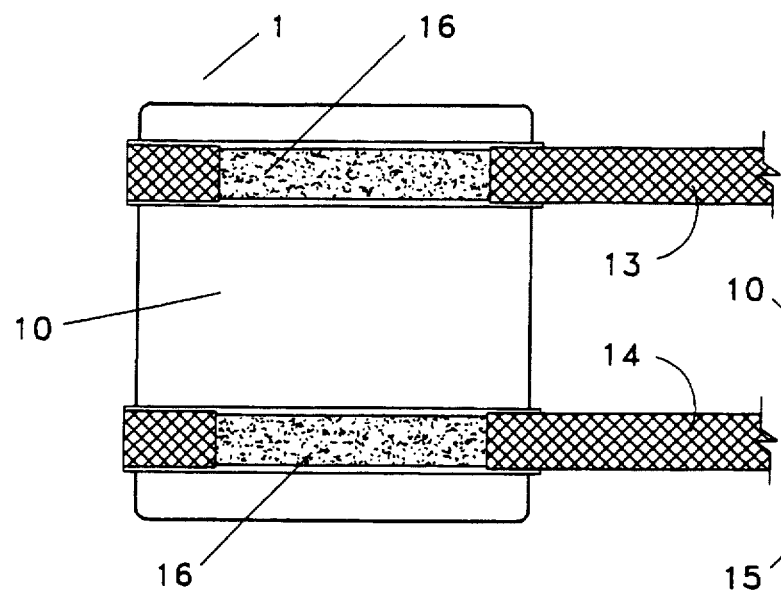
FIG. 1 is a top view of the preferred embodiment of the bandage.
Figure 2:
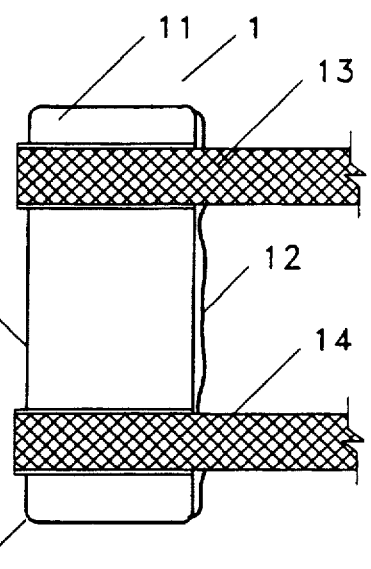
FIG. 2 is a lateral view of the preferred embodiment of the bandage.
Figure 3:
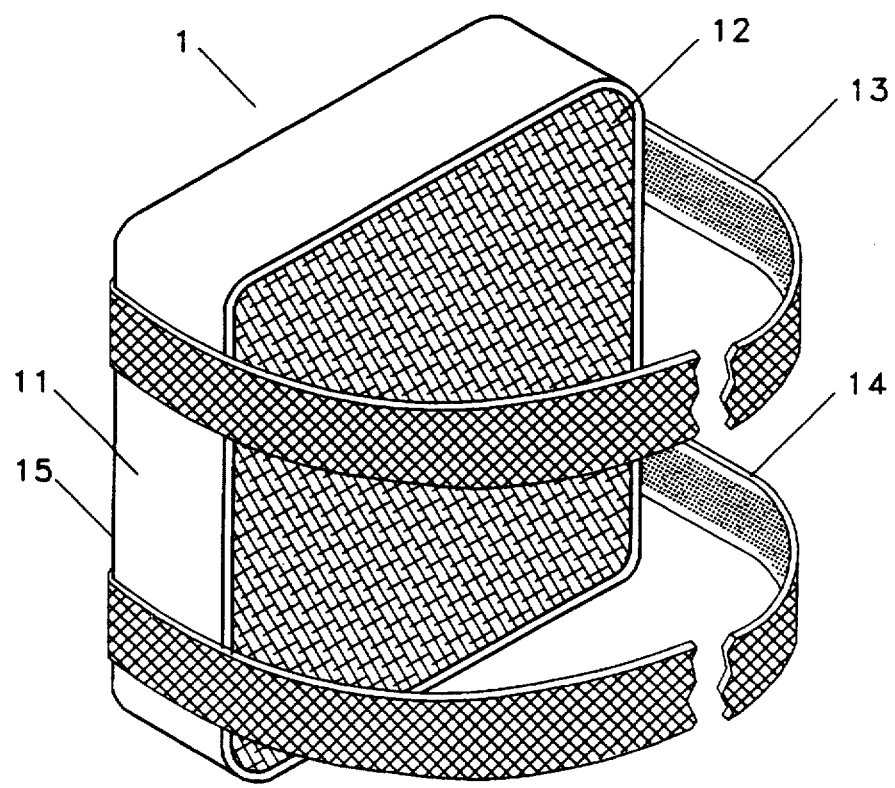
FIG. 3. is a bottom view of the preferred embodiment of the bandage.

FIGS. 1, 2 and 3 represent drawings of a preferred embodiment of a compress type bandage 1 for staunching wound bleeding while preventing or reducing transmission of blood borne pathogens from a bleeding wound area to a person applying the bandage to the wound. The primary elements of the bandage are a planar, non-porous first layer having a first side and a second side opposite the first 10, a sidewall of the first layer 11 which serves as a holding means for the person administering the bandage, a gauze pad second layer having a first side and a second side opposite the first 12, the first side of the gauze pad layer affixed to the second side of the non-porous layer 10 and one or a plurality of flexible straps 13 and 14 which are affixed to the first side of the non-porous layer 10 and sidewall 11.

In FIG. 1, the bandage 1 contains a planar, non-porous first layer 10 having a first side and a second side opposite the first, that is impermeable to blood and body fluid and can be sterilized. The impermeable material should be sufficiently firm to apply a staunching pressure to the wound when secured, yet flexible enough so that the material contours the body area where the wound is located. Under the preferred embodiment of the invention, the non-porous layer 10 should be made of a material such as polypropylene or polyurethane. Polypropylene is particularly appropriate in medical applications because it provides a barrier to water and fat soluble materials, it is malleable, it can be manufactured into various shapes by means of injection molding process (which is particularly useful in the manufacture of the invention's finger units) and it can be sterilized. The preferred thickness of the non-porous layer 10, if made of polypropylene, should be between 0.050 inches to 0.080 inches. By applying these dimensions, the non-porous layer 10 is malleable allowing it to contour to the wound area and yet has firmness sufficient to apply pressure to the wound when secured to the wound area by means of a strap 13 and 14.

In FIG. 2, the planar, non-porous first layer 10, having edges on the first side 15, has a sidewall 11 which extends continuously and perpendicularly from the first layer 10. The sidewall 11 and the edges 15 of the first layer 10 serve as a holding or gripping means for the person administering emergency aid. The sidewall 11 further provides distancing between the first layer 10 and the gauze pad material 12 to lessen unintended exposure to blood and body fluids from a wound. As an alternative embodiment, the holding means 11 and 15 can be enhanced with striations or finger grooves located on the sidewalls 11 and the edges 15 of the first layer 10 to serve as a gripping means.

In FIG. 3, a gauze dressing pad 12 second layer having a first side and a second side opposite the first, the first side of the gauze pad is affixed to the second side of the non-porous layer 10 and between the sidewalls 11. The gauze pad material 12 can be affixed to the second side of the non-porous layer 10 with adhesives. The gauze pad 12 typically would be comprised of standard cotton dressing material which will directly contact the wound, is highly absorbent of human blood and body fluid, and can be sterilized.

In FIG. 1, a flexible strap having a first side and a second side opposite the first and having a first end with a second end opposite the first 13 of substantial longitudinal elasticity to allow the strap to extend and wrap around the wound area and be secured in such a way so as to retain the bandage on the wounded area, the first side of the strap is affixed by the first end to the first side of the first layer 10. Parallel to the flexible strap 13 can be a second flexible strap having a first side and a second side opposite the first 14 which likewise is affixed to the first side of the first layer 10. In FIG. 2, as an alternative embodiment, the flexible straps 13 and 14 similarly may be affixed to the sidewall 11. The straps 13 and 14 are affixed to the first layer 10 and sidewalls 11 preferably by means of adhesives. As shown in FIG. 3, the flexible straps 13 and 14 are of substantial longitudinal elasticity to extend and wrap around the wound. The straps are then secured to retain the bandage on the wounded area. The flexible straps 13 and 14 can be selected from various types of material, such as hook and loop tape fastener such as those sold under the registered trademark "Velcro"®, nylon tape, cotton ties or rubber.

The closure of the straps to retain and compress the bandage on the wounded area is accomplished with a fastening means 16, preferably a hook and loop fastener such as those sold under the registered trademark "Velcro"® in which the Velcro® can be affixed to the straps 13 and 14 by means of adhesives, or fastened with double-sided closing tape. As an alternative embodiment, the straps 13 and 14, if made of cotton or elastic rubber, can be tied to secure the bandage.

Figure 4:
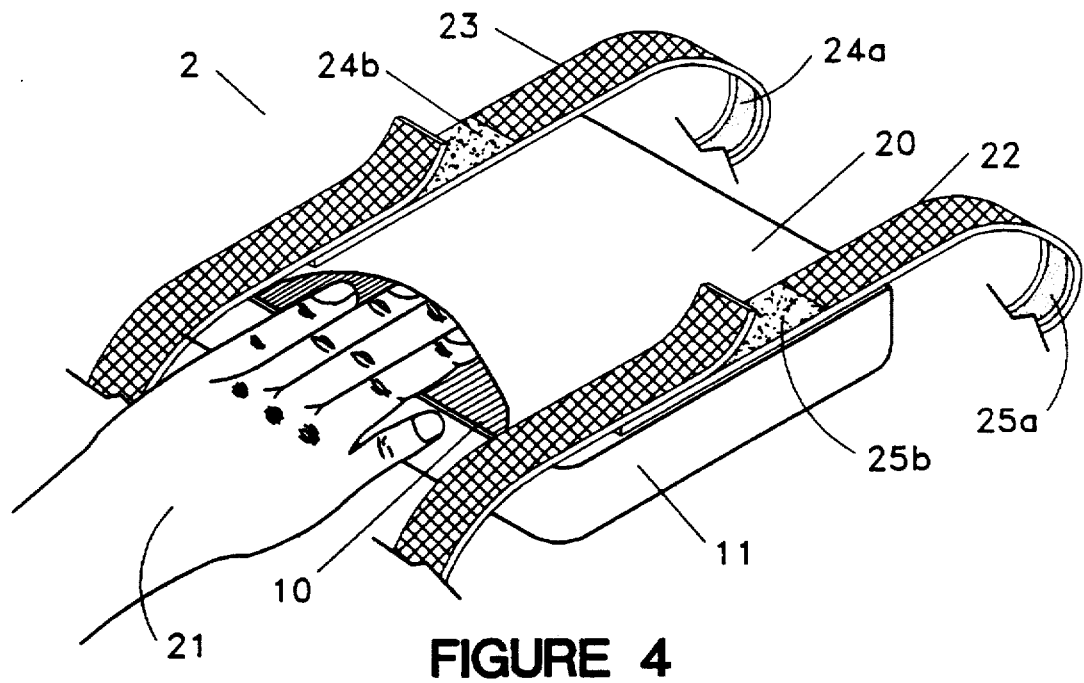
FIG. 4 demonstrates an alternate embodiment of the bandage for larger area wounds as shown from above.

In an alternative embodiment, FIG. 4 shows the bandage 2 in which the holding means is in the form of a non-porous hood or roof 20 which is affixed to the first layer 10, but open on one end 21 to form a sleeve or mitten. The person who is administering emergency aid can slide his or her hand into the sleeve or hood 20 of the bandage 2 through the opening 21 which would serve as a holding means while the person administers the bandage to the bleeding wound.

As shown in FIG. 4, a flexible strap having a first side and a second side opposite the first 22 of substantial longitudinal elasticity to allow the strap to extend and wrap around the wound area and be secured in such a way so as to retain the bandage on the wounded area, the first side of the strap is affixed to the first side of the first layer 10. Parallel to the flexible strap 22 can be a second flexible strap having a first side and a second side opposite the first 23 which likewise is affixed to the first side of the first layer 10. The closure of the straps to retain and compress the bandage on the wounded area is accomplished with a fastening means 24a and 24b and 25a and 25b, preferably a hook and loop fastener such as Velcro®. As shown in FIG. 4, the hook portion 24a of the fastening means, which is affixed to the first side of the strap 23, is secured to the loop portion 24b of the fastening means which is affixed to the second side of the strap 23. Likewise, the hook portion 25a of the fastening means, which is affixed to the first side of the strap 22, is secured to the loop portion 25b of the fastening means which is affixed to the second side of the strap 22.

Figure 5:
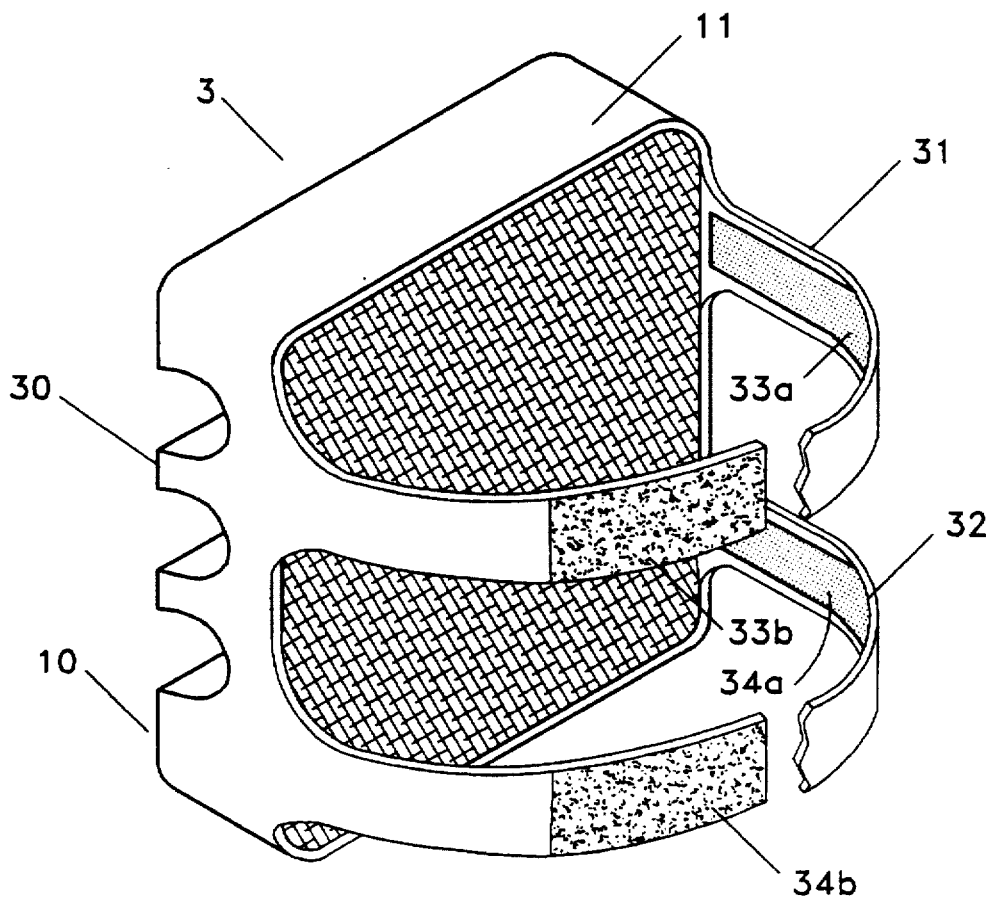
FIG. 5 portrays an alternate embodiment of the bandage as viewed from below.

FIG. 5 further portrays an alternative embodiment of the bandage 3 in which the holding means can be enhanced by a gripping means 30 in the form of finger grooves, or, as shown in FIG. 5, a handle which can be molded as part of the first side of the first layer 10. FIG. 5 further represents an alternative embodiment of the bandage 3 in which flexible straps 31 and 32 are molded as part of the non-porous material used for the first layer 10 and sidewalls 11. The flexible straps 31 and 32 having first sides and second sides opposite the first extend longitudinally beyond the sidewall 11 and are secured to the wounded area by a fastening means 33a and 33b and 34a and 34b which are affixed to the straps 31 and 32 and can be comprised of material such as Velcro®, double-sided taped and closing tape, or snaps. FIG. 5 shows the use of a hook and loop nylon tape such as Velcro® as a fastening means to retain and compress the bandage 3 on the wounded area. Under this embodiment, a hook portion 33a of the fastening means, which is affixed to the first side of the strap 31, is secured to a loop portion 33b of the fastening means which is affixed to the second side of the strap 31. Likewise, a hook portion 34a of the fastening means, which is affixed to the first side of the strap 32, is secured to a loop portion 34b of the fastening means which is affixed to the second side of the strap 32.

Figure 6:
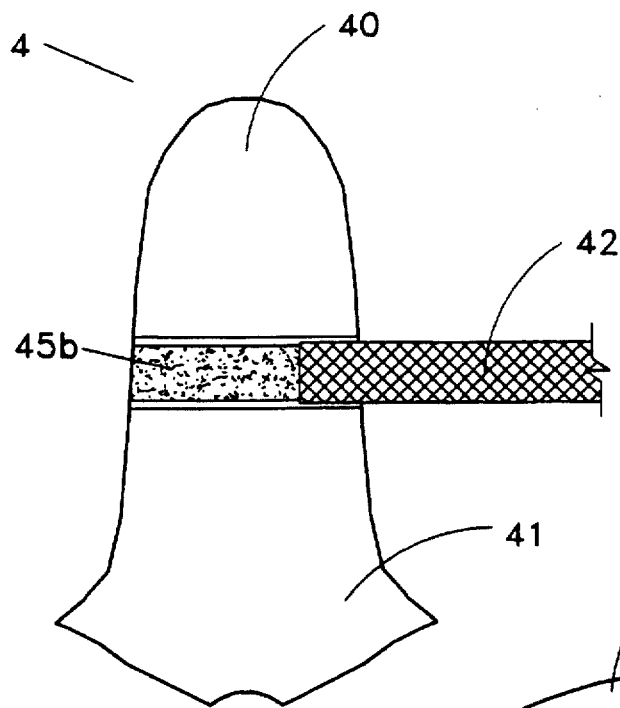
FIG. 6 portrays an alternate embodiment of the bandage for fingers as shown from above.
Figure 7:
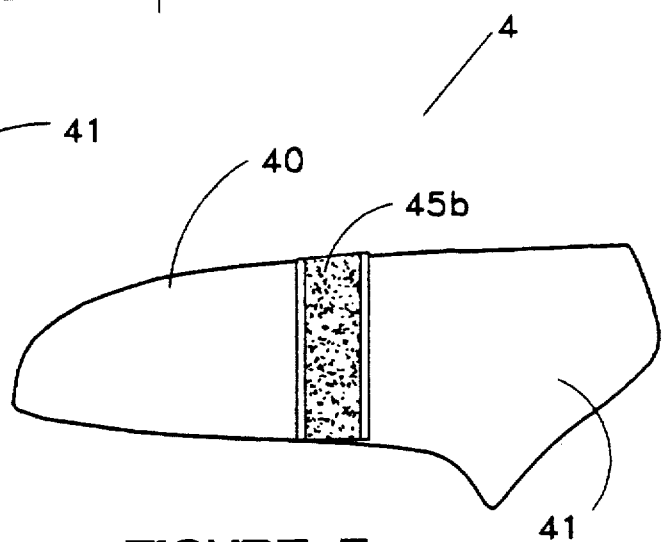
FIG. 7 portrays a lateral view of an alternate embodiment of the bandage for fingers.
Figure 8:
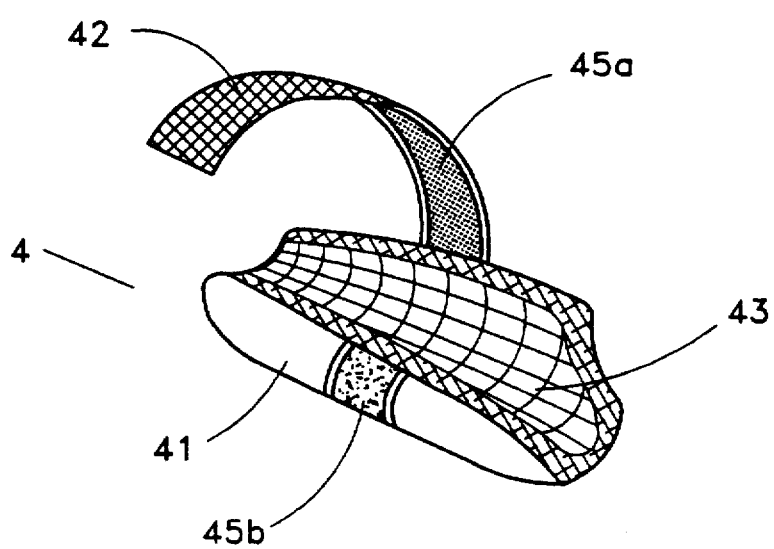
FIG. 8 demonstrates an alternate embodiment of the bandage for fingers as shown from below.

FIG. 6, 7 and 8 show the preferred embodiment of the bandage for finger wounds. FIG. 6 shows a bandage 4 which contains a non-porous first layer 40 having a first side and a second side opposite the first that is impermeable to body fluid. In FIG. 7, the non-porous first layer 40 is concave in shape and curves downward along two sidewalls 41 from the first side of the non-porous layer 40. The curvature of the non-porous layer 40 should be made of a firm, yet flexible, substance such as polypropylene or polyurethane. Polypropylene is particularly appropriate in medical applications because it provides a barrier to water and fat soluble materials, it is malleable, it can molded into shapes (which is particularly useful in the manufacture of the invention's finger units) and it can be sterilized.

The preferred thickness of the non-porous first layer 40, if made of polypropylene, should be between 0.050 inches to 0.080 inches. By applying these dimensions, the non-porous layer 40 is malleable to contour to the wound area and yet has sufficient firmness to apply pressure to the wound if affixed to the wound area by means of a flexible strap 42.

In FIG. 8, an absorbent gauze dressing pad second layer 43 having a first side and a second side opposite the first side, the first side of the second layer 40 is affixed to the second side of the non-porous layer 40 and between the sidewalls 41. The gauze dressing pad material 43 would be comprised of standard cotton dressing material that can absorb human blood and can be sterilized.

In FIG. 6, a flexible strap 42 having a first side and a second side opposite the first side, the first side of the strap is affixed to the first side of the first layer 40. As shown in FIG. 8, the flexible strap 42 is of substantial longitudinal elasticity to extend and wrap around the wound. The flexible strap can be selected from various types of materials, such as hook and loop nylon tape fastener, nylon tape, cotton ties or rubber. The strap 42 is then secured by a fastening means 45a and 45b, such as Velcro®, double-sided closing tape, or by tying to retain and compress the bandage on the wounded area. FIG. 8 shows the use of nylon hook and loop tape such as Velcro® as an embodiment of the fastening means. The loop portion 45a of the fastening means, which is affixed to the first side of the strap 42, is secured to the hook portion 45b of the fastening means which is affixed to the first side of the first layer 40. As an alternative, the flexible strap 42 can be molded as part of the non-porous material which makes up the sidewall 41 and extend longitudinally beyond the sidewall 41 and secured to the wounded area by means of Velcro®, double-sided closure tape or snaps.

The preferred embodiments of the invention would have the following dimensions:

| Size | Hood Size | Dressing Size | Strap | Appropriate Wound |
| --- | --- | --- | --- | --- |
| Finger | 3.25 × 1.5" | 3.25 × 1.5" | 35 cm × 2.5 | Finger |
| Small | 3 × 2.5" | 2 "× 2" | 35 cm × 2.5 | hand, wrist, forearm |
| Medium | 5 × 4.5" | 4 "× 4" | 40 cm × 2.5 | neck, shoulder |
| Large | 7 × 6.5" | 6 "× 6" | 50 cm × 2.5 | lower extremity |
| X-Large | 10 × 10" | 8 "× 8" | 70 cm × 5 | chest/abdomen |

As will be understood, the shape, the size and the number of layers contained in the bandage can be varied as desired and as necessary. Each bandage is sterilized and then individually wrapped in a sterilized package, preferably, a paper product.

Under the preferred embodiment of the invention, and with reference in particular to FIG. 1, 2 and 3, a person who will administer emergency aid can unwrap the bandage 1 from its sterilized package, preferably paper, grab the bandage 1 at the holding means 11 and 15 and then apply the bandage 1 to the wound in which the absorbent gauze pad material 12 would make direct contact with the wound. The first layer 10 and sidewall 11 is intended to isolate the hand of the person applying the bandage from contact with blood from a wound. The gauze then could be secured and compressed to the wound by wrapping the flexible straps 13 and 14 around the wounded area and securing the straps 13 and 14 with a fastening means 16. Once secured, the bandage also would serve as a compress.

In summary, the emergency dressing has the following, essential characteristics or advantages:

(a) It can be used by any one without special training.

(b) The invention precludes the need for multiple products to protect the administrator of emergency aid from exposure to bloodborne pathogens. The inventive bandage dispels the need for placing, packaging and using separate gauze, separate gloves and separate surgical adhesive tape. The invention would reduce the costs of having to purchase multiple products. The invention simply is removed from its sterilized wrapping and applied immediately to the wound.

(c) It will reduce the cost of manufacturing, by requiring a limited number of main components, i.e., the non-porous layer which doubles as a gripping or holding means, the gauze pad material, the straps, and, in larger bandages, a protective sleeve.

(d) The non-porous first layer and sidewall serve as a holding means to reduce the risk of unintended exposure to blood and body fluid from the wound.

(e) The combination of semi-flexible non-porous layer in conjunction with the flexible straps enables the person administering emergency aid to secure the bandage on the wound and allow the bandage to serve as a compress.

Although a preferred embodiment has been described above, the scope of the invention is limited only by the following claims:

We claim:

1. A multi-layered bandage for preventing or reducing transmission of blood borne pathogens from a bleeding wound area to a person applying the bandage to the wound, comprising:

a. A planar, non-porous first layer having a first side and a second side opposite the first, the first layer constructed of non-porous material that is impermeable to blood and body fluid, and sufficiently flexible to contour the wound area, and sufficiently firm to apply staunching pressure to the wound when pressed or secured to the wound area, and the first side of the non-porous first layer serves as a gripping means in the form of a plurality of finger grooves formed into the first side of the first layer wherein said grooves are parallel to each other and whereby the hand of the person applying the bandage is prevented from contacting blood from the wound;

b. a second layer, having a first side and a second side opposite the first, comprising material absorbent of blood and body fluid, the first side of the second layer affixed to the second side of the non-porous first layer;

c. a flexible strap having a first side and a second side opposite the first, and having a first end with a second end opposite the first, of substantial longitudinal elasticity to allow the strap to extend and wrap around the wound area and be secured, the first side of the strap is affixed by the first end to the first side of the first layer; and d. a fastening means affixed to the second end of the strap and constructed of material to allow the strap to retain and compress the bandage on the wounded area.

2. A multi-layered bandage of claim 1, the non-porous first layer is comprised of a material such as polypropylene or polyurethane having a thickness between 0.050 inches to 0.080 inches.

3. A multi-layered bandage of claim 1, in which the flexible strap is comprised of a nylon hook and loop fastening tape.

4. A multi-layered bandage of claim 1, in which the flexible strap is comprised of a cotton material.

5. A multi-layered bandage of claim 1, in which the flexible strap is comprised of a soft, pliable rubber material.

6. A multi-layered bandage of claim 1, in which the flexible strap is comprised of the same non-porous material as the first layer.

7. A multi-layered bandage of claim 1, in which the fastening means is a nylon, hook and loop tape.

8. A multi-layered bandage of claim 1, in which the fastening means is double-sided adhesive tape.

9. A multi-layered bandage for preventing or reducing transmission of blood borne pathogens from a bleeding wound area to a person applying the bandage to the wound, comprising:

a. A planar, non-porous first layer having a first side and a second side opposite the first, the first layer constructed of non-porous material that is impermeable to blood and body fluid, and sufficiently flexible to contour the wound area, and sufficiently firm to apply staunching pressure to the wound when pressed or secured to the wound area;

b. a second layer, having a first side and a second side opposite the first, comprising material absorbent of blood and body fluid, the first side of the second layer affixed to the second side of the non-porous first layer;

c. a flexible strap having a first side and a second side opposite the first, and having a first end with a second end opposite the first, of substantial longitudinal elasticity to allow the strap to extend and wrap around the wound area and be secured, the first side of the strap is affixed by the first end to the first side of the first layer;

d. a fastening means affixed to the second end of the strap and constructed of material to allow the strap to retain and compress the bandage on the wounded area; and e. a gripping means in the form of a plurality of finger grooves that are parallel to each other and affixed to the first side of the first layer whereby the hand of the person applying the bandage is prevented from contacting blood from the wound.

10. A multi-layered bandage of claim 9, in which the gripping means is comprised of a material such as polypropylene or polyurethane having a thickness between 0.050 inches to 0.080 inches.

11. A multi-layered bandage of claim 9, in which the flexible strap is comprised of a nylon hook and loop fastening tape.

12. A multi-layered bandage of claim 9, in which the flexible strap is comprised of a cotton material.

13. A multi-layered bandage of claim 9, in which the flexible strap is comprised of a soft, pliable rubber material.

14. A multi-layered bandage of claim 9, in which the flexible strap is comprised of the same non-porous material as the first layer.

15. A multi-layered bandage of claim 9, in which the fastening means is a nylon, hook and loop tape.

16. A multi-layered bandage of claim 9, in which the fastening means is double-sided adhesive tape.

17. A multi-layered bandage for preventing or reducing transmission of blood borne pathogens from a bleeding wound area to a person applying the bandage to the wound, comprising:
 a. A planar, non-porous first layer having a first side and a second side opposite the first, the first layer constructed of non-porous material that is impermeable to blood and body fluid, and sufficiently flexible to contour the wound area, and sufficiently firm to apply staunching pressure to the wound when pressed or secured to the wound area;
 b. a second layer, having a first side and a second side opposite the first, comprising material absorbent of blood and body fluid, the first side of the second layer affixed to the second side of the non-porous first layer;
 c. a flexible strap having a first side and a second side opposite the first, and having a first end with a second end opposite the first, of substantial longitudinal elasticity to allow the strap to extend and wrap around the wound area and be secured, the first side of the strap is affixed by the first end to the first side of the first layer;
 d. a fastening means affixed to the second end of the strap and constructed of material to allow the strap to retain and compress the bandage on the wounded area; and
 e. a gripping means in which the gripping means is a roof or hood affixed to the first side of the first layer to form a mitten or sheath for the hand of the bandage applicant whereby the hand of the person applying the bandage is prevented from contacting blood from the wound.

18. A multi-layered bandage of claim 17, in which the non-porous first layer is comprised of a material such as polypropylene or polyurethane having a thickness between 0.050 inches to 0.080 inches.

19. A multi-layered bandage of claim 17, in which the flexible strap is comprised of a cotton material or nylon hook and loop fastening tape.

20. A multi-layered bandage of claim 17, in which the flexible strap is comprised of a soft, pliable rubber material.

21. A multi-layered bandage of claim 17, in which the flexible strap is comprised of the same non-porous material as the first layer.

22. A multi-layered bandage of claim 17, in which the fastening means is a nylon, hook and loop tape.

23. A multi-layered bandage of claim 17, in which the fastening means is double-sided adhesive tape.

24. A method for preventing or reducing transmission of blood borne pathogens from a bleeding wound area to a person applying the bandage to the wound, the method comprising:
 a. providing a bandage comprising a planar, non-porous first layer having a first side and a second side opposite the first, the first layer constructed of non-porous material that is impermeable to blood and body fluid, and sufficiently flexible to contour the wound area, and sufficiently firm to apply staunching pressure to the wound when pressed or secured to the wound area, and further comprising a gripping means in which the gripping means is a roof or hood affixed to the first side of the first layer to form a mitten or sheath for the hand of the bandage applicant whereby the hand of the person applying the bandage is prevented from contacting blood from the wound, the bandage further comprising a second layer, having a first side and a second side opposite the first, comprising material absorbent of blood and body fluid, the first side of the second layer affixed to the second side of the non-porous first layer, the bandage further comprising a flexible strap having a first side and a second side opposite the first, and having a first end with a second end opposite the first, of substantial longitudinal elasticity to allow the strap to extend and wrap around the wound area and be secured, the first side of the strap is affixed by the first end to the first side of the first layer; and a fastening means affixed to the second end of the strap and constructed of material to allow the strap to retain and compress the bandage on the wounded area;
 b. entering the applicant's hand into the mitten of the gripping means and gripping the bandage;
 c. positioning the bandage to cover the wound area by use of the gripping means and thereby placing the second layer, comprising material absorbent of blood and body fluid, over the wound preventing or reducing transmission of blood borne pathogens from the bleeding wound area to a bandage applicant;
 d. applying pressure to the wound by pressing the bandage against the wound;
 e. wrapping the flexible strap around the wound area, placing tension on the strap to allow it to be secured and compressed on the wound area; and
 f. securing the flexible strap by the fastening means.

\* \* \* \* \*

UNITED STATES PATENT AND TRADEMARK OFFICE
CERTIFICATE OF CORRECTION

PATENT NO.   : 5,558,918
DATED        : September 24, 1996
INVENTOR(S)  : Chrisanne Gordon, et al It is certified that error appears in the above-indentified patent and that said Letters Patent is hereby corrected as shown below:

On the cover page, above the Abstract, the acknowledgment of Attorney, Agent, Firm is missing and should read as follows: --Attorney, Agent, Firm - John G. Dirina, Esq.-- .

Column 3, line 28 in the Summary of the Invention, delete beginning "opposite the first the first side" and replace with --opposite the first. The first side-- .

Column 8, line 26, for claim reference numeral 7, delete the duplicative "nylon, hook and loop tape." and replace with --nylon tape.-- as supported in the specification column 5, line 2. The duplication was inadvertant and nylon tape does not add new matter to the claim(s).

Column 9, line 7, for claim reference numeral 15, delete "nylon, hook and loop tape." as inadvertantly duplicative and replace with --nylon tape.--. In Column 9, line 37, claim 17, delete "a mitten or sheath for the hand" and replace with --a mitten or sheath for insertion of the hand-- , as such clarification was requested by the Examiner during prosecution of the patent.

Column 10, line 2, for claim reference numeral 22, delete " nylon, hook and loop tape." and replace with -- nylon tape. --.

Signed and Sealed this

Tenth Day of December, 1996

Attest:

BRUCE LEHMAN

*Attesting Officer*     Commissioner of Patents and Trademarks